(12) United States Patent
Notte

(10) Patent No.: US 9,333,197 B2
(45) Date of Patent: May 10, 2016

(54) APOPTOSIS SIGNAL-REGULATING KINASE INHIBITOR

(71) Applicant: Gregory Notte, Foster City, CA (US)

(72) Inventor: Gregory Notte, Foster City, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 14/254,359

(22) Filed: Apr. 16, 2014

(65) Prior Publication Data

US 2014/0228412 A1    Aug. 14, 2014

Related U.S. Application Data

(62) Division of application No. 13/748,901, filed on Jan. 24, 2013, now Pat. No. 8,742,126.

(60) Provisional application No. 61/591,710, filed on Jan. 27, 2012.

(51) Int. Cl.
| | |
|---|---|
| *A61K 31/44* | (2006.01) |
| *C07D 213/56* | (2006.01) |
| *A61K 31/4439* | (2006.01) |
| *C07D 401/14* | (2006.01) |
| *C07D 233/56* | (2006.01) |
| *C07D 401/04* | (2006.01) |

(52) U.S. Cl.
CPC .......... *A61K 31/4439* (2013.01); *C07D 213/56* (2013.01); *C07D 233/56* (2013.01); *C07D 401/04* (2013.01); *C07D 401/14* (2013.01)

(58) Field of Classification Search
None
See application file for complete search history.

(56) References Cited

U.S. PATENT DOCUMENTS

| | | |
|---|---|---|
| 8,263,595 B2 | 9/2012 | Swinnen et al. |
| 8,378,108 B2 | 2/2013 | Corkey et al. |
| 2008/0223996 A1 | 10/2006 | Sun et al. |

(Continued)

FOREIGN PATENT DOCUMENTS

| | | |
|---|---|---|
| EP | 2058309 A1 | 5/2009 |
| WO | WO-2008042867 A2 | 4/2008 |

(Continued)

OTHER PUBLICATIONS

Formentini et al (Nephrol Dial Transplant, 2012; 27(Supple 3):iii81-iii88).*

(Continued)

*Primary Examiner* — Marcos Sznaidman
*Assistant Examiner* — Rayna B Rodriguez

(57) ABSTRACT

The present invention relates to a compound of formula (I):

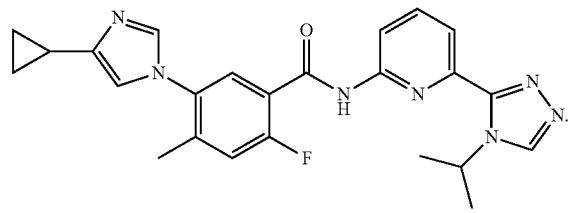

The compound has apoptosis signal-regulating kinase ("ASK1") inhibitory activity, and is thus useful in the treatment of diseases such as kidney disease, diabetic nephropathy and kidney fibrosis.

21 Claims, 2 Drawing Sheets

(56) References Cited

U.S. PATENT DOCUMENTS

| | | |
|---|---|---|
| 2007/0167386 A1 | 7/2007 | Otsu et al. |
| 2007/0276050 A1 | 11/2007 | Koch et al. |
| 2009/0318425 A1 | 12/2009 | Chang et al. |
| 2010/0029619 A1 | 2/2010 | Uchikawa et al. |
| 2011/0009410 A1 | 1/2011 | Corkey et al. |
| 2012/0004267 A1 | 1/2012 | Corkey et al. |

FOREIGN PATENT DOCUMENTS

| | | |
|---|---|---|
| WO | WO-2009011850 A2 | 1/2009 |
| WO | WO-2009027283 A1 | 3/2009 |
| WO | WO-2009123986 A1 | 10/2009 |
| WO | WO-2010111464 A1 | 9/2010 |
| WO | WO-2011041293 A1 | 4/2011 |
| WO | WO-2012068464 A2 | 5/2012 |
| WO | WO-2012080735 A1 | 6/2012 |
| WO | WO-2013/006485 A1 | 1/2013 |

OTHER PUBLICATIONS

Guo, Xiaoli et al. (2010) "Regulation of the Severity of Neuroinflammation and demyelination by TLR-ASL1-p38 Pathway" *EMBO Molecular Medicine* (1):1-12.

'Guo, Xiaoli et al. (2010) "Regulation of the Severity of Neuroinflammation and demyelination by TLR-ASL1-p38 Pathway" Supporting Information: 1-25.

Hattori, K. et al. (2009) "The roles of ASK family proteins in stress responses and diseases", Cell Communication and Signaling, 7:9 pp. 1-10.

Ichijo, H. et al. (1997) "Induction of Apoptosis by ASK1, a Mammalian MAPKKK that Activates SAPK/JNK and p38 Signaling Pathways", Science, vol. 275, pp. 90-94.

International Search Report for PCT/US2010/041739, International Filing Date Jul. 12, 2010, mailed Sep. 16, 2010.

International Search Report for PCT/US2011/042694, international filing date Jun. 30, 2011, mailed Aug. 22, 2011.

Iriyama, T. et al. (2009), "ASK1 and ASK2 differently regulate the counteracting roles of apoptosis and inflammation in tumorigensis", The European Molecular Biology Organization Journal, pp. 1-11.

Kumar, S. et al. (2003) "P38 Map Kinases: Key Singalling Molecules as Therapeutic Targets for Inflammatory Disease", Nature Reviews, vol. 2, pp. 717-726.

Mnich, S. et al (2010) "Critical Role for Apoptosis Signal-regulating Kinase 1 in the Development of Inflammatory K/BxN Serum-induced Arthritis" *International Immunopharmacology* (10): 1170-1176.

Nagai, H. et al. (2007) "Pathophysiological Roles of ASK-1 MAP Kinase Signaling Pathways", Journal of Biochemistry and Molecular Biology, vol. 40, pp. 1-6.

Okamoto, M. et al (2010) "Identification of Novel ASK1 Inhibitors Using Virtual Screening" *Bioorganic & Medicinal Chemistry*, 1-4.

Pimienta, G. et al. (2007) "Canonical and Alternative MAPK Signaling", Cell Cycle, vol. 6(21), pp. 2628-2632.

Saitoh, M. et al. (1998), "Mammalian thioredoxin is a direct inhibitor of apoptosis signal-regulating kinase (ASK) 1", The European Molecular Biology Organization Journal, vol. 17(9), pp. 2596-2606.

Takeda, K. et al. (2007), "Apoptosis Signal-regulating Kinase (ASK) 2 Functions as a Mitogen-activated Protein Kinase Kinase Kinase in a Heteromeric Complex with ASK1", Journal of Biological Chemistry, vol. 282(10), pp. 7522-7531.

Takeda, K. (2008) "Apoptosis Signal-Regulating Kinase 1 in Stress and Immune Response", Annu. Rev. Pharmacol. Toxicol., 48:8.1-8.27.

Volynets et al. (2010) "Identification of $3H$-Naphtho[1,2,3-*de*]quinoline-2,7-diones as Inhibitors of Apoptosis Signal-Regulating Kinase 1 (ASK1)" *Journal of Medicinal Chemistry*:1-7.

Wang, Z.S. et al. (1998), "MAPKKK6, a Novel Mitogen-Activated protein Kinase Kinase Kinase, That Associates with MAPKKK5", Biochemical and Biophysical Research Communications, vol. 253, pp. 33-37.

Written Opinion for International Application No. PCT/US2010/041739, International Filing Date, Jul. 12, 2010, mailed Sep. 16, 2010.

Zhang, L. et al. (1999), "Suppression of apoptosis signal-regulating kinase 1-induced cell death by 14-3-3 proteins", Proc. Natl. Sci, vol. 96, pp. 8511-8515.

International Search Report for PCT/US13/022997.

Knittel J and Zavod R. Drug Design and Relationship of Functional Groups to Pharmacological Activity; Foye's Principles of Medicinal Chemistry, 5th Edition, Lippincott Williams & Wilkins; ed. David A. Williams and Thomas L. Lernke; 2002; 37-67.

Patani GA and LaVoie EJ. Biososterism: A Rational Approach in Drug Design. Chem. REv. 1996, 96, 3147-3146.

Restriction Requirement issued on Jan. 9, 2015 for U.S. Appl. No. 14/254,359, filed on Apr. 16, 2014 (9 pages).

Office Action dated Oct. 21, 2014 for Pakistan Patent Application No. 39/2013 (2 pages).

Office Action dated May 4, 2015 for New Zealand Appl. No. 627947.

Office Action dated May 8, 2015 for Philippines Appl. No. 1-2014-501697.

Office Action dated Jul. 6, 2015 for Chinese Appl. No. 201380006957.0.

Office Action dated Jul. 14, 2015 for U.S. Appl. No. 14/254,359.

Office Action dated Jul. 17, 2015 for Korean Appl. No. 10-2014-7023533.

Office Action dated Mar. 19, 2015 for Taiwan Patent Application No. 103125752 (3 pages) Translated. (*Corrected* cite adding "date" from previous Supplemental IDS dated Apr. 9, 2015).

Office Action dated Sep. 7, 2015 for Eurasian Patent Application No. 201491283/28 (2 pages).

Office Action dated Aug. 3, 2015 for Chile Appl. No. 01988-2014.

\* cited by examiner

APOPTOSIS SIGNAL-REGULATING KINASE INHIBITOR

CROSS-REFERENCE TO RELATED APPLICATIONS

This application claims priority to U.S. Provisional Patent Application Ser. No. 61/591,710, filed Jan. 27, 2012, the entirety of which is incorporated herein by reference.

FIELD OF THE INVENTION

The present invention relates to a novel compound for use in the treatment of ASK1-mediated diseases. The invention also relates to intermediates for its preparation and to pharmaceutical compositions containing said novel compound.

BACKGROUND

Apoptosis signal-regulating kinase 1 (ASK1) is a member of the mitogen-activated protein kinase kinase kinase ("MAP3K") family that activates the c-Jun N-terminal protein kinase ("JNK") and p38 MAP kinase (Ichijo, H., Nishida, E., Irie, K., Dijke, P. T., Saitoh, M., Moriguchi, T., Matsumoto, K., Miyazono, K., and Gotoh, Y. (1997) *Science*, 275, 90-94). ASK1 is activated by a variety of stimuli including oxidative stress, reactive oxygen species (ROS), LPS, TNF-α, FasL, ER stress, and increased intracellular calcium concentrations (Hattori, K., Naguro, I., Runchel, C., and Ichijo, H. (2009) *Cell Comm. Signal.* 7:1-10; Takeda, K., Noguchi, T., Naguro, I., and Ichijo, H. (2007) *Annu. Rev. Pharmacol. Toxicol.* 48: 1-8.27; Nagai, H., Noguchi, T., Takeda, K., and Ichijo, I. (2007) *J. Biochem. Mol. Biol.* 40:1-6). Phosphorylation of ASK1 protein can lead to apoptosis or other cellular responses depending on the cell type. ASK1 activation and signaling have been reported to play an important role in a broad range of diseases including neurodegenerative, cardiovascular, inflammatory, autoimmune, and metabolic disorders. In addition, ASK1 has been implicated in mediating organ damage following ischemia and reperfusion of the heart, brain, and kidney (Watanabe et al. (2005) *BBRC* 333, 562-567; Zhang et al., (2003) Life Sci 74-37-43; Terada et al. (2007) *BBRC* 364: 1043-49).

ROS are reported be associated with increases of inflammatory cytokine production, fibrosis, apoptosis, and necrosis in the kidney. (Singh D K, Winocour P, Farrington K. Oxidative stress in early diabetic nephropathy: fueling the fire. *Nat Rev Endocrinol* 2011 March; 7(3):176-184; Brownlee M. Biochemistry and molecular cell biology of diabetic complications. Nature 2001 Dec. 13; 414(6865):813-820; Mimura I, Nangaku M. The suffocating kidney: tubulointerstitial hypoxia in end-stage renal disease. *Nat Rev Nephrol* 2010 November; 6(11):667-678).

Moreover, oxidative stress facilitates the formation of advanced glycation end-products (AGEs) that cause further renal injury and production of ROS. (Hung K Y, et al. N-acetylcysteine-mediated antioxidation prevents hyperglycemia-induced apoptosis and collagen synthesis in rat mesangial cells. *Am J Nephrol* 2009; 29(3):192-202).

Tubulointerstitial fibrosis in the kidney is a strong predictor of progression to renal failure in patients with chronic kidney diseases (Schainuck L I, et al. Structural-functional correlations in renal disease. Part II: The correlations. *Hum Pathol* 1970; 1: 631-641.). Unilateral ureteral obstruction (UUO) in rats is a widely used model of tubulointerstitial fibrosis. UUO causes tubulointerstital inflammation, increased expression of transforming growth factor beta (TGF-β), and accumulation of myofibroblasts, which secrete matrix proteins such as collagen and fibronectin. The UUO model can be used to test for a drug's potential to treat chronic kidney disease by inhibiting renal fibrosis (Chevalier et al., Ureteral obstruction as a model of renal interstitial fibrosis and obstructive nephropathy, *Kidney International* (2009) 75, 1145-1152.

Thus, therapeutic agents that function as inhibitors of ASK1 signaling have the potential to remedy or improve the lives of patients in need of treatment for diseases or conditions such as neurodegenerative, cardiovascular, inflammatory, autoimmune, and metabolic disorders. In particular, ASK1 inhibitors have the potential to treat cardio-renal diseases, including kidney disease, diabetic kidney disease, chronic kidney disease, fibrotic diseases (including lung and kidney fibrosis), respiratory diseases (including chronic obstructive pulmonary disease (COPD) and acute lung injury), acute and chronic liver diseases.

U.S. Publication No. 2007/0276050 describes methods for identifying ASK1 inhibitors useful for preventing and/or treating cardiovascular disease and methods for preventing and/or treating cardiovascular disease in an animal.

WO2009027283 discloses triazolopyridine compounds, methods for preparation thereof and methods for treating autoimmune disorders, inflammatory diseases, cardiovascular diseases and neurodegenerative diseases.

U.S. Patent Publication No. 2001/00095410A1, published Jan. 13, 2011, discloses compounds useful as ASK-1 inhibitors. U.S. Patent Publication 2001/00095410A1 relates to compounds of Formula (I):

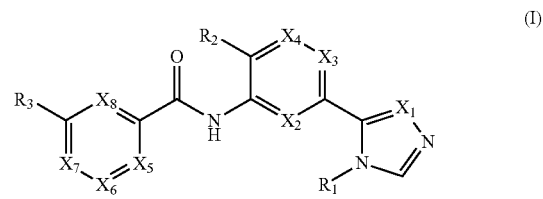

wherein:
$R^1$ is alkyl, alkenyl, alkynyl, cycloalkyl, aryl, heteroaryl, or heterocyclyl, all of which are optionally substituted with 1, 2, or 3 substituents selected from halo, oxo, alkyl, cycloalkyl, heterocyclyl, aryl, aryloxy, —$NO_2$, $R^6$, —C(O)—$R^6$, —OC(O)—$R^6$—C(O)—O—$R^6$, —C(O)—N($R^6$)($R^7$), —OC(O)—N($R^6$)($R^7$), —S—$R^6$, —S(=O)$_2R^6$, —S(=O)$_2$—N($R^6$)($R^7$), —S(=O)$_2$—O—$R^6$, —N($R^6$)($R^7$), —N($R^6$)—C(O)—$R^7$, —N($R^6$)—C(O)—O—$R^7$, —N($R^6$)—C(O)—N($R^6$)($R^7$), —N($R^6$)—S(=O)$_2$—$R^6$, —CN, and —O—$R^6$,
wherein alkyl, cycloalkyl, heterocyclyl, phenyl, and phenoxy are optionally substituted by 1, 2, or 3 substituents selected from alkyl, cycloalkyl, alkoxy, hydroxyl, and halo; wherein $R^6$ and $R^7$ are independently selected from the group consisting of hydrogen, $C_1$-$C_{15}$ alkyl, cycloalkyl, heterocyclyl, aryl, and heteroaryl, all of which are optionally substituted with 1-3 substituents selected from halo, alkyl, mono- or dialkylamino, alkyl or aryl or heteroaryl amide, —CN, lower alkoxy, —$CF_3$, aryl, and heteroaryl; or
$R^6$ and $R^7$ when taken together with the nitrogen to which they are attached form a heterocycle;
$R^2$ is hydrogen, halo, cyano, alkoxy, or alkyl optionally substituted by halo;
$R^3$ is aryl, heteroaryl, or heterocyclyl, all of which are optionally substituted with one or more substituents selected from alkyl, alkoxy, cycloalkyl, cycloalkylalkyl, aryl, arylalkyl, heteroaryl, heteroarylalkyl, heterocyclyl, heterocyclylalkyl, halo, oxo, —$NO_2$, haloalkyl, haloalkoxy, —CN, —O—$R^6$, —O—C(O)—$R^6$, —O—C(O)—N($R^6$)($R^7$), —S—$R^6$, —N($R^6$)($R^7$), —S(=O)—$R^6$, —S(=O)$_2R^6$, —S(=O)$_2$—N($R^6$)($R^7$), —S(=O)$_2$—O—$R^6$, —N($R^6$)—C(O)—$R^7$, —N($R^6$)—C(O)—O—$R^7$, —N($R^6$)—C(O)—N($R^6$)($R^7$), —C(O)—$R^6$, —C(O)—O—$R^6$, —C(O)—N($R^6$)($R^7$), and —N($R^6$)—S(=O)$_2$—$R^7$, wherein the alkyl, alkoxy, cycloalkyl, aryl, heteroaryl or heterocyclyl is further optionally substituted with one or more substituents selected from halo, oxo, —$NO_2$, alkyl, haloalkyl, haloalkoxy, —N($R^6$)($R^7$), —C(O)—$R^6$, —C(O)—O—$R^6$, —C(O)—N($R^6$)($R^7$), —CN, —O—$R^6$, cycloalkyl, aryl, heteroaryl and heterocyclyl;

with the proviso that the heteroaryl or heterocyclyl moiety includes at least one ring nitrogen atom;

$X^1, X^2, X^3, X^4, X^5, X^6, X^7$ and $X^8$ are independently C($R^4$) or N, in which each $R^4$ is independently hydrogen, alkyl, alkoxy, cycloalkyl, aryl, heteroaryl, heterocyclyl, halo, —$NO_2$, haloalkyl, haloalkoxy, —CN, —O—$R^6$, —S—$R^6$, —N($R^6$)($R^7$), —S(=O)—$R^6$, —S(=O)$_2R^6$, —S(=O)$_2$—N($R^6$)($R^7$), —S(=O)$_2$—O—$R^6$, —N($R^6$)—C(O)—$R^7$, —N($R^6$)—C(O)—O—$R^7$, —N($R^6$)—C(O)—N($R^6$)($R^7$), —C(O)—$R^6$, —C(O)—O—$R^6$, —C(O)—N($R^6$)($R^7$), or —N($R^6$)—S(=O)$_2$—$R^7$, wherein the alkyl, cycloalkyl, aryl, heteroaryl, and heterocyclyl is further optionally substituted with one or more substituents selected from halo, oxo, —$NO_2$, —$CF_3$, —O—$CF_3$, —N($R^6$)($R^7$), —C(O)—$R^6$, —C(O)—O—$R^7$, —C(O)—N($R^6$)($R^7$), —CN, —O—$R^6$; or $X^5$ and $X^6$ or $X^6$ and $X^7$ are joined to provide optionally substituted fused aryl or optionally substituted fused heteroaryl; and with the proviso that at least one of $X^2, X^3$, and $X^4$ is C($R^4$); at least two of $X^5, X^6, X^7$, and $X^8$ are C($R^4$); and at least one of $X^2, X^3, X^4, X^5, X^6, X^7$ and $X^8$ is N.

The above disclosures notwithstanding, there is a need for compounds that are potent and exhibit improved pharmacokinetic and/or pharmacodynamic profiles for the treatment of diseases related to ASK1 activation.

Surprisingly, applicants have discovered a novel compound within the scope of U.S. patent publication US2011/0009410A exhibiting good potency, improved pharmacokinetic and/or pharmacodynamic profiles, on aggregate, compared to compounds disclosed therein.

SUMMARY OF THE INVENTION

The present invention relates to a compound of the formula:

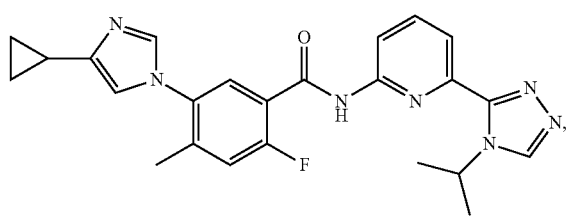

(I)

or a pharmaceutically acceptable salt thereof.

In one embodiment, the invention relates to the use of a compound of formula (I) in the treatment of a disease in a patient in need of treatment with an ASK1 inhibitor.

In another embodiment, the invention relates to a pharmaceutical composition comprising a compound of formula (I) or a pharmaceutically acceptable salt thereof, and one or more pharmaceutically acceptable carriers.

In another embodiment, the invention is a method of treating diabetic nephropathy, or complications of diabetes, comprising administering a therapeutically effective amount of a compound of formula (I) or a pharmaceutically acceptable salt thereof, to a patient in need thereof.

In another embodiment, the invention relates to a method of treating kidney disease, or diabetic kidney disease comprising administering a therapeutically effective amount of a compound of formula (I) or a pharmaceutically acceptable salt thereof, to a patient in need thereof.

In another embodiment, the invention relates to a method of treating kidney fibrosis, lung fibrosis, or idiopathic pulmonary fibrosis (IPF) comprising administering a therapeutically effective amount of a compound of formula (I) or a pharmaceutically acceptable salt thereof, to a patient in need thereof.

In another embodiment, the invention relates to a method of treating diabetic kidney disease, diabetic nephropathy, kidney fibrosis, liver fibrosis, or lung fibrosis comprising administering a therapeutically effective amount of a compound or salt of formula (I), to a patient in need thereof.

In another embodiment, the invention relates to intermediates useful for the synthesis of the compound of formula (I).

In another embodiment, the invention relates to the use of a compound of formula (I) or a pharmaceutically acceptable salt thereof for the treatment of chronic kidney disease.

In another embodiment, the invention relates to the use of a compound of formula (I) or a pharmaceutically acceptable salt thereof for the treatment of diabetic kidney disease.

In another embodiment, the invention relates to the use of a compound of formula (I) or a pharmaceutically acceptable salt thereof, in the manufacture of a medicament for the treatment of chronic kidney disease.

In yet another embodiment, the invention relates to the compound of formula (I) for use in therapy.

DETAILED DESCRIPTION OF THE INVENTION

Figures

DEFINITIONS AND GENERAL PARAMETERS

Figure 1:
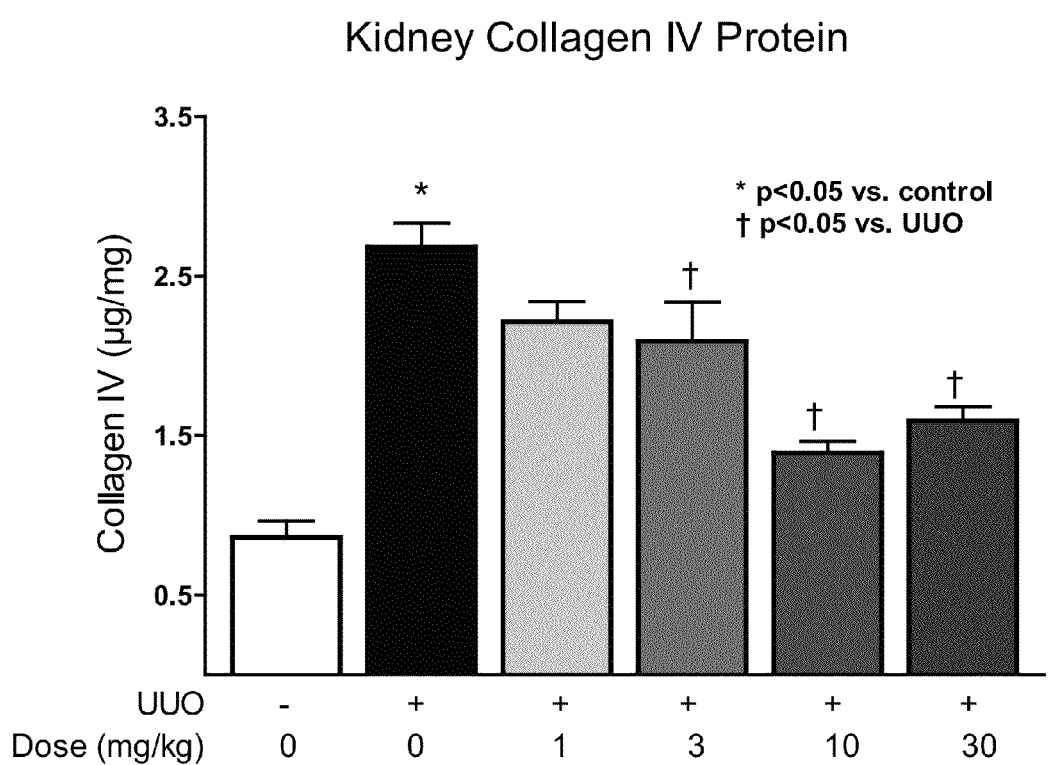
FIG. 1 is a bar graph showing the levels of Collagen IV in the kidney cortex of rats subjected to seven days of unilateral ureteral obstruction and treated with either vehicle, or compound of formula (I) at 1, 3, 10, or 30 mg/kg b.i.d. per day.

As used herein, the following words and phrases are intended to have the meanings set forth below, except to the extent that the context in which they are used indicates otherwise. Where no indication or definition is given, the ordinary meaning of the word or phrase as found in a relevant dictionary or in common usage known to one of skill in the art is implied.

The term "chronic kidney disease" as used herein refers to progressive loss of kidney function over time typically months or even years. Chronic kidney disease (CKD) is diagnosed by a competent care giver using appropriate information, tests or markers known to one of skill in the art. Chronic kidney disease includes by implication kidney disease.

The term "diabetic kidney disease" as used herein refers to kidney disease caused by diabetes, exacerbated by diabetes, or co-presenting with diabetes. It is a form of chronic kidney disease occurring in approximately 30% of patients with diabetes. It is defined as diabetes with the presence of albuminuria and/or impaired renal function (i.e. decreased glomerular filtration rate (See. de B, I, et al. Temporal trends in the prevalence of diabetic kidney disease in the United States. *JAMA* 2011 Jun. 22; 305(24):2532-2539).

The term "pharmaceutically acceptable salt" refers to salts of pharmaceutical compounds e.g. compound of formula (I) that retain the biological effectiveness and properties of the underlying compound, and which are not biologically or otherwise undesirable. There are acid addition salts and base addition salts. Pharmaceutically acceptable acid addition salts may be prepared from inorganic and organic acids.

Acids and bases useful for reaction with an underlying compound to form pharmaceutically acceptable salts (acid addition or base addition salts respectively) are known to one of skill in the art. Similarly, methods of preparing pharmaceutically acceptable salts from an underlying compound (upon disclosure) are known to one of skill in the art and are disclosed in for example, Berge, at al. *Journal of Pharmaceutical Science*, January 1977 vol. 66, No. 1, and other sources. Salts derived from inorganic acids include but are not limited to hydrochloric acid, hydrobromic acid, sulfuric acid, nitric acid, phosphoric acid, and the like. Salts derived from organic acids include but are not limited to maleic acid, fumaric acid, tartaric acid, p-toluene-sulfonic acid, and the like. Bases useful for forming base addition salts are known to one of skill in the art. An example of a pharmaceutically acceptable salt of the compound of formula (I) is the hydrochloride salt of the compound of formula (I).

As used herein, "pharmaceutically acceptable carrier" includes excipients or agents such as solvents, diluents, dispersion media, coatings, antibacterial and antifungal agents, isotonic and absorption delaying agents and the like that are not deleterious to the compound of the invention or use thereof. The use of such carriers and agents to prepare compositions of pharmaceutically active substances is well known in the art (see, e.g., Remington's *Pharmaceutical Sciences*, Mace Publishing Co., Philadelphia, Pa. 17th Ed. (1985); and *Modern Pharmaceutics*, Marcel Dekker, Inc. 3rd Ed. (G. S. Banker & C. T. Rhodes, Eds.)

The term "cardio-renal diseases" as used herein refers to diseases, related to the function of the kidney, that are caused or exacerbated by cardiovascular problems such as, for example, high blood pressure or hypertension. It is believed that hypertension is a major contributor to kidney disease.

The term "respiratory diseases" as used herein refers to diseases including chronic obstructive pulmonary disease (COPD) and idiopathic pulmonary fibrosis (IPF).

The term "therapeutically effective amount" refers to an amount of the compound of formula (I) that is sufficient to effect treatment as defined below, when administered to a patient (particularly a human) in need of such treatment in one or more doses. The therapeutically effective amount will vary, depending upon the patient, the disease being treated, the weight and/or age of the patient, the severity of the disease, or the manner of administration as determined by a qualified prescriber or care giver.

The term "treatment" or "treating" means administering a compound or pharmaceutically acceptable salt of formula (I) for the purpose of:
(i) delaying the onset of a disease, that is, causing the clinical symptoms of the disease not to develop or delaying the development thereof;
(ii) inhibiting the disease, that is, arresting the development of clinical symptoms; and/or
(iii) relieving the disease, that is, causing the regression of clinical symptoms or the severity thereof.

In a preferred embodiment, the invention relates to the use of the compound of formula (I) in treating chronic kidney disease comprising administering a therapeutically effective amount to a patient in need thereof.

In another preferred embodiment the invention relates to the use of the compound of formula (I) in treating diabetic kidney disease comprising administering a therapeutically effective amount to a patient in need thereof.

In another preferred embodiment the invention relates to the use of the compound of formula (I) in treating lung or kidney fibrosis comprising administering a therapeutically effective amount to a patient in need thereof.

The half maximal inhibitory concentration ($IC_{50}$) of a therapeutic agent is the concentration of a therapeutic agent necessary to produce 50% of the maximum inhibition against a target enzyme. It is a desirable goal to discover a therapeutic agent, for example a compound that inhibits apoptosis signal-regulating kinase (ASK1) with a low $IC_{50}$. In this manner, undesirable side effects are minimized by the ability to use a lower dose of the therapeutic agent to inhibit the ASK1 enzyme.

Similarly, it is a desirable goal to discover a therapeutic agent that has a low dissociation constant ($K_d$). $K_d$ is used to describe the affinity between a ligand (such as a therapeutic agent) and the corresponding kinase or receptor; i.e. a measure of how tightly a therapeutic agent binds to a particular kinase, for example the apoptosis signal-regulating kinase ASK1. Thus, a lower $K_d$ is generally preferred in drug development.

Similarly, it is a desirable goal to discover a compound having a low $EC_{50}$. $EC_{50}$ is the concentration of a drug that achieves 50% maximal efficacy in the cell. The $EC_{50}$ value translates to the concentration of a compound in the assay medium necessary to achieve 50% of the maximum efficacy. Thus, a lower $EC_{50}$ is generally preferred for drug development. A useful unit of measure associated with $EC_{50}$ is the protein binding adjusted $EC_{50}$ ($PB_{adj}.EC_{50}$ as used herein). This value measures the amount of a drug e.g. compound of formula (I) correlated to the fraction of the drug that is unbound to protein which provides 50% maximal efficacy. This value measures the efficacy of the drug corrected for or correlated to the amount of drug that is available at the target site of action.

Another desirable property is having a compound with a low cell membrane efflux ratio as determined by CACO cell permeability studies. An efflux ratio ((B/A)/(A/B)) less than 3.0 is preferred. A compound with a ratio greater than 3 is expected to undergo active rapid efflux from the cell and may not have sufficient duration in the cell to achieve maximal efficacy.

Another desirable goal is to discover a drug that exhibits minimal off-target inhibition. That is, a drug that minimally inhibits the Cyp450 (cytochrome p450) enzymes. More particularly, a drug that is a weak inhibitor of cyp3A4, the most important of the P450 enzymes, is desired. A weak inhibitor is a compound that causes at least 1.25-fold but less than 2-fold increase in the plasma AUC values, or 20-50% decrease in clearance (wikipedia.org/wiki/cyp3A4, visited 11/12/11). Generally, a compound exhibiting a Cyp3A4 $IC_{50}$ of greater than 10 uM is considered a weak inhibitor.

A measure useful for comparing cyp3A4 inhibition among drug candidates is the ratio of Cyp3A4 inhibition and the protein binding adjusted $EC_{50}$. This value gives an indication of the relative potential for cyp inhibition corrected for the protein binding adjusted $EC_{50}$ which is specific to each drug. A higher ratio in this measure is preferred as indicative of lower potential for cyp3A4 inhibition.

Unexpectedly and advantageously, applicants have discovered a compound (of formula (I) herein) within the generic scope of U.S. Patent publication No. 2001/00095410A1 that provides advantages compared to structurally close compounds (herein designated as compounds A and B) disclosed in U.S. Patent publication No. 2001/00095410A1

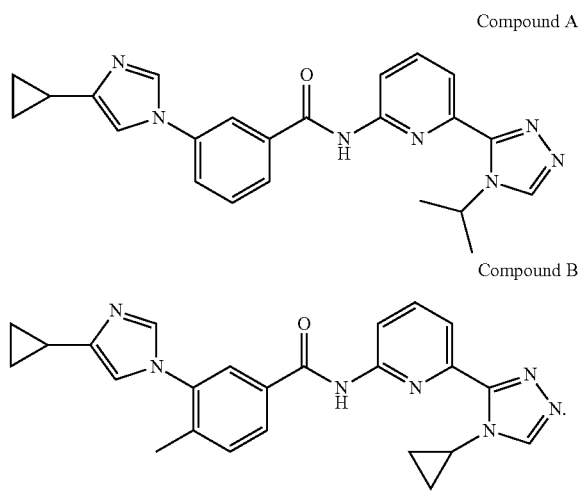

Compound A

Compound B

Therefore, objects of the present invention include but are not limited to the provision of a compound of formula (I) or pharmaceutically acceptable salt thereof, and methods of using the compound of formula (I) for the treatment of kidney disease, chronic kidney disease, diabetic kidney disease, diabetic nephropathy, kidney fibrosis or lung fibrosis.

Combination Therapy

Patients being treated for cardio-renal diseases such as chronic kidney disease may benefit from combination drug treatment. For example the compound of the present invention may be combined with one or more of angiotensin converting enzyme (ACE) inhibitors such as enalapril, captopril, ramipril, lisinopril, and quinapril; or angiontesin II receptor blockers (ARBs) such as losartan, olmesartan, and irbesartan; or antihypertensive agents such as amlodipine, nifedipine, and felodipine. The benefit of combination may be increased efficacy and/or reduced side effects for a component as the dose of that component may be adjusted down to reduce its side effects while benefiting from its efficacy augmented by the efficacy of the compound of formula (I) and/or other active component(s).

Patients presenting with chronic kidney disease treatable with ASKI inhibitors such as compound of formula (I), may also exhibit conditions that benefit from co-administration (as directed by a qualified caregiver) of a therapeutic agent or agents that are antibiotic, analgesic, antidepressant and/or anti-anxiety agents in combination with compound of formula (I). Combination treatments may be administered simultaneously or one after the other within intervals as directed by a qualified caregiver or via a fixed dose (all active ingreditents are combined into the a single dosage form e.g. tablet) presentation of two or more active agents.

Pharmaceutical Compositions and Administration

The compound of the present invention may be administered in the form of a pharmaceutical composition. The present invention therefore provides pharmaceutical compositions that contain, as the active ingredient, the compound of formula (I), or a pharmaceutically acceptable salt thereof, and one or more pharmaceutically acceptable excipients and/or carriers, including inert solid diluents and fillers, diluents, including sterile aqueous solution and various organic solvents, permeation enhancers, solubilizers and adjuvants. The pharmaceutical compositions may be administered alone or in combination with other therapeutic agents. Compositions may be prepared for delivery as solid tablets, capsules, caplets, ointments, skin patches, sustained release, fast disintegrating tablets, inhalation preparations, etc. Typical pharmaceutical compositions are prepared and/or administered using methods and/or processes well known in the pharmaceutical art (see, e.g., Remington's *Pharmaceutical Sciences*, Mace Publishing Co., Philadelphia, Pa. 17th Ed. (1985); and *Modern Pharmaceutics*, Marcel Dekker, Inc. 3rd Ed. (G. S. Banker & C. T. Rhodes, Eds.).

Formulations for combination treatments comprising the compound of formula (I) may be presented as fixed dose formulations e.g. tablets, elixirs, liquids, ointments, inhalants, gels, etc., using procedures known to one of skill in the art.

Pharmaceutical compositions of the compound of formula (I) may be administered in either single or multiple doses by routes including, for example, rectal, buccal, intranasal and transdermal routes; by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer. Most preferred routes of administration include oral, parental and intravenous administration.

The compound of formula (I) may be administered in a pharmaceutically effective amount. For oral administration, each dosage unit preferably contains from 1 mg to 500 mg of the compound of formula (I). A more preferred dose is from 1 mg to 250 mg of the compound of formula (I). Particularly preferred is a dose of the compound of formula (I) ranging from about 20 mg twice a day to about 50 mg twice a day. It will be understood, however, that the amount of the compound actually administered usually will be determined by a physician in light of the relevant circumstances including the condition to be treated, the chosen route of administration, co-administration compound if applicable, the age, weight, response of the individual patient, the severity of the patient's symptoms, and the like.

Nomenclature

The name of the compound of the present invention as generated using ChemBioDraw Ultra 11.

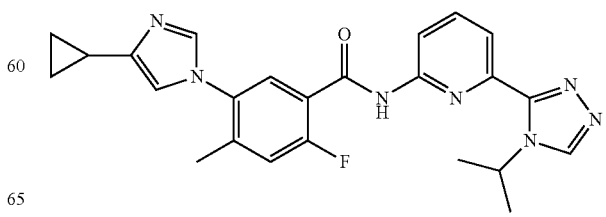

is 5-(4-cyclopropyl-1H-imidazol-1-yl)-N-(6-(4-isopropyl-4H-1,2,4-triazol-3-yl)pyridin-2-yl)-2-fluoro-4-methylbenzamide also known as 5-((4-cyclopropyl-1H-imdazol-1-yl)-2-fluoro-N-(6-(4-isopropyl-4H-1,2,4-triazole-3-yl)pyridine-2-yl)-4-methylbenzamide.

Synthesis of the Compound of Formula (I)

The compound of the invention may be prepared using methods disclosed herein or modifications thereof which will be apparent given the disclosure herein. The synthesis of the compound of the invention may be accomplished as described in the following example. If available, reagents may be purchased commercially, e.g. from Sigma Aldrich or other chemical suppliers. Alternatively, reagents may be prepared using reaction schemes and methods known to one of skill in the art.

Synthetic Reaction Parameters

The terms "solvent," "inert organic solvent" or "inert solvent" refer to a solvent inert under the conditions of the reaction being described in conjunction therewith (including, for example, benzene, toluene, acetonitrile, tetrahydrofuran (THF), dimethylformamide (DMF), chloroform, methylene chloride (or dichloromethane), diethyl ether, petroleum ether (PE), methanol, pyridine, ethyl acetate (EA) and the like. Unless specified to the contrary, the solvents used in the reactions of the present invention are inert organic solvents, and the reactions are carried out under an inert gas, preferably nitrogen.

One method of preparing compounds of formula (I) is shown in Reaction Schemes 1 and 2 below.

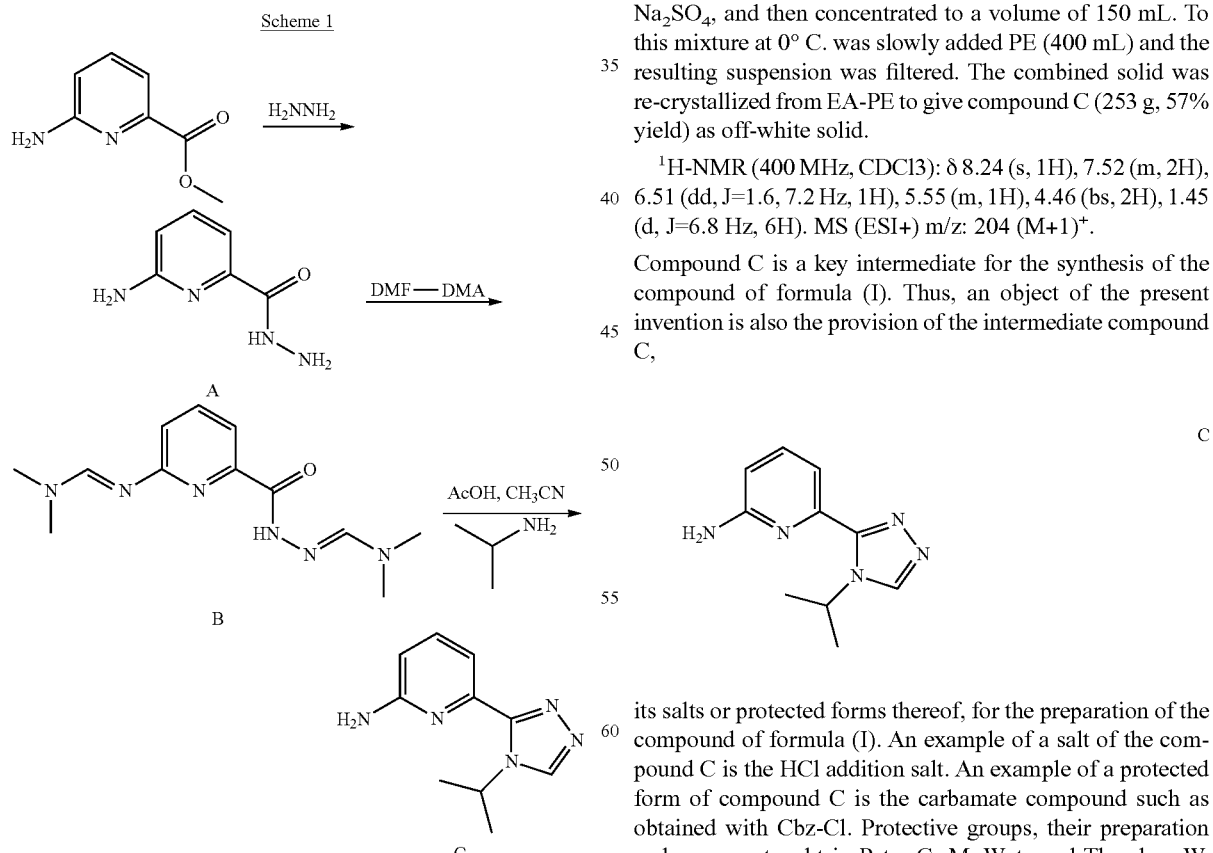

Preparation of Compound A

To a solution of methyl 6-aminopicolinate (432 g, 2.84 mol) in MeOH (5 L) was added $NH_2NH_2 \cdot H_2O$ (284 g, 5.68 mol, 2.0 eq.). The reaction mixture was heated under reflux for 3 hr and then cooled to room temperature. The precipitate formed in the mixture was collected by filtration, washed with EA (2 L×2) and then dried in vacuo to give compound A (405 g, 94% yield) as white solid.

Preparation of Compound B

A mixture of compound A (405 g, 2.66 mol) in dimethylformamide-dimethylacetal (DMF-DMA) (3.54 L) was heated under reflux for 18 hr, cooled to room temperature and then concentrated under reduced pressure. The residue was taken up in EA (700 mL) and heated at 50° C. for 20 min. After being cooled to room temperature, the solid was collected by filtration and dried in vacuo to give compound B (572 g, 82% yield) as white solid.

Preparation of C

To a solution of compound B (572 g, 2.18 mol) in a mixture of $CH_3CN$—AcOH (3.6 L, 4:1) was added propan-2-amine (646 g, 5.0 eq.). The resulting mixture was heated under reflux for 24 hr and then cooled to room temperature, and the solvent was removed under reduced pressure. The residue was dissolved in water (2.8 L) and 1 N aqueous NaOH was added to a pH of 8.0 H. The precipitate was collected by filtration and the filtrate was extracted with EA (500 mL×3). The combined organic layers were dried over anhydrous $Na_2SO_4$, and then concentrated to a volume of 150 mL. To this mixture at 0° C. was slowly added PE (400 mL) and the resulting suspension was filtered. The combined solid was re-crystallized from EA-PE to give compound C (253 g, 57% yield) as off-white solid.

$^1$H-NMR (400 MHz, CDCl3): δ 8.24 (s, 1H), 7.52 (m, 2H), 6.51 (dd, J=1.6, 7.2 Hz, 1H), 5.55 (m, 1H), 4.46 (bs, 2H), 1.45 (d, J=6.8 Hz, 6H). MS (ESI+) m/z: 204 (M+1)$^+$.

Compound C is a key intermediate for the synthesis of the compound of formula (I). Thus, an object of the present invention is also the provision of the intermediate compound C,

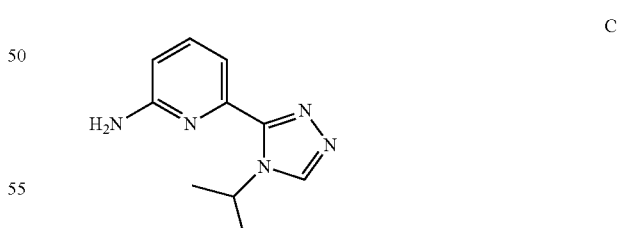

its salts or protected forms thereof, for the preparation of the compound of formula (I). An example of a salt of the compound C is the HCl addition salt. An example of a protected form of compound C is the carbamate compound such as obtained with Cbz-Cl. Protective groups, their preparation and uses are taught in Peter G. M. Wuts and Theodora W. Greene, *Protective Groups in Organic Chemistry*, 2$^{nd}$ edition, 1991, Wiley and Sons, Publishers.

Scheme 2

Preparation of the Compound of formula (I) continued:

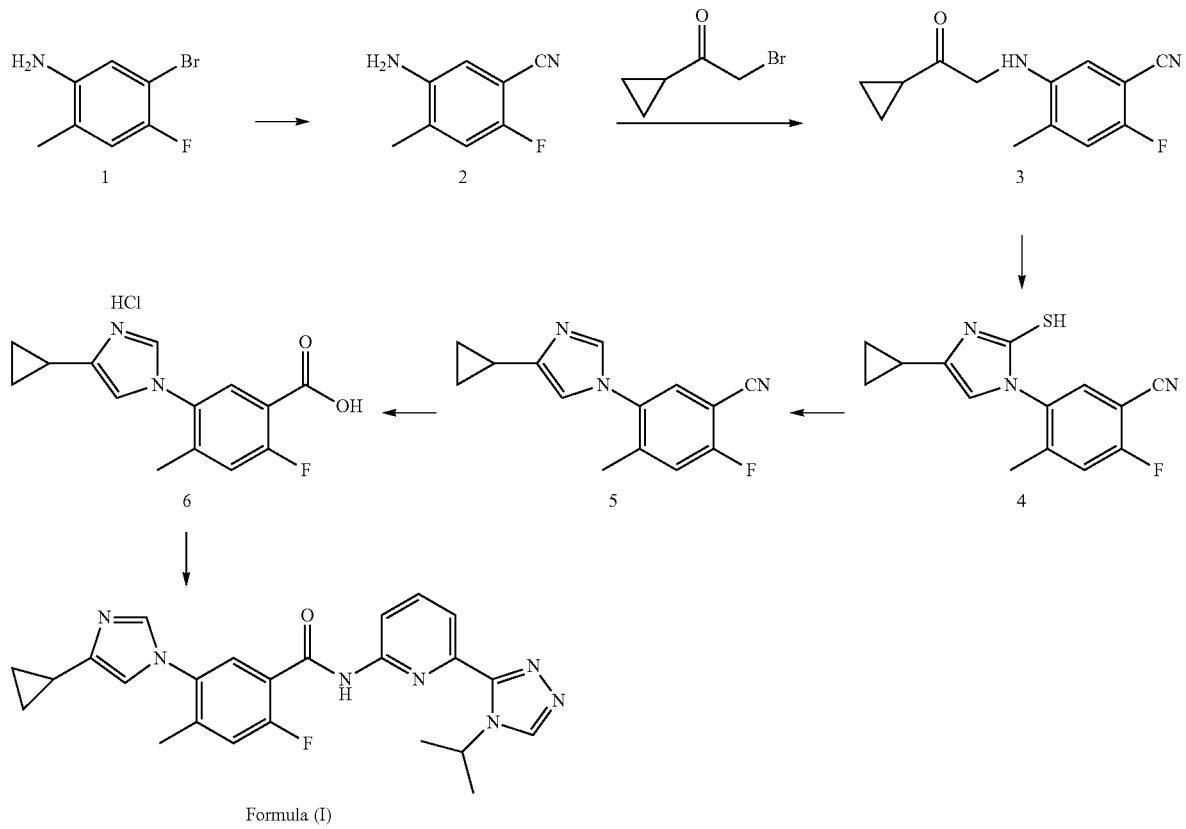

Formula (I)

Compound 6 is a key intermediate for the synthesis of the compound of formula (I). Thus an object of the present invention is also the provision of intermediate compound 6,

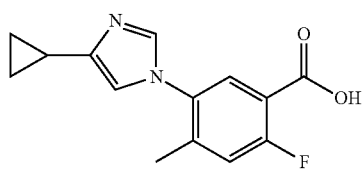

6 salts or protected forms thereof, for the preparation of the compound of formula (I). An example of a salt of the compound 6 is the HCl addition salt. An example of a protected form of the compound 6 is an ester (e.g. methyl, ethyl or benzyl esters) or the carbamate compound such as obtained with Cbz-Cl. Protective groups, their preparations and uses are taught in Peter G. M. Wuts and Theodora W. Greene, *Protective Groups in Organic Chemistry*, 2$^{nd}$ edition, 1991, Wiley and Sons, Publishers.

Step 1—Preparation of 5-amino-2-fluoro-4-methyl-benzonitrile—Compound (2)

The starting 5-bromo-4-fluoro-2-methylaniline (1) (20 g, 98 mmol) was dissolved in anhydrous 1-methylpyrrolidinone (100 mL), and copper (I) cyanide (17.6 g, 196 mmol) was added. The reaction was heated to 180° C. for 3 hours, cooled to room temperature, and water (300 mL) and concentrated ammonium hydroxide (300 mL) added. The mixture was stirred for 30 minutes and extracted with EA (3×200 mL). The combined extracts were dried over magnesium sulfate, and the solvent was removed under reduced pressure. The oily residue was washed with hexanes (2×100 mL), and the solid dissolved in dichloromethane and loaded onto a silica gel column. Eluting with 0 to 25% EA in hexanes gradient provided 5-amino-2-fluoro-4-methylbenzonitrile (10.06 g, 67.1 mmol). LC/MS (m/z: 151 M$^{+1}$).

Step 2—Preparation of 5-(2-cyclopropyl-2-oxoethylamino)-2-fluoro-4-methylbenzonitrile—Compound (3)

5-Amino-2-fluoro-4-methylbenzonitrile (12 g, 80 mmol) was dissolved in anhydrous N,N-dimethylformamide (160 mL) under nitrogen, and potassium carbonate (13.27 g, 96 mmol) and potassium iodide (14.61 g, 88 mmol) were added as solids with stirring. The reaction was stirred for 5 minutes at room temperature and then bromomethyl cyclopropylketone (20.24 mL, 180 mmol) was added. The reaction mixture was heated to 60° C. for 3 hours, and then the solvents removed under reduced pressure. The residue was dissolved in EA (400 mL) and washed with 400 mL of water. The organic layer was dried over magnesium sulfate, and solvent was removed under reduced pressure. The residue was re-dissolved in a minimum amount of EA, and hexanes were added to bring the solution to 3:1 hexanes:EA by volume. The product precipitated out of solution and was collected by filtration to provide 5-(2-cyclopropyl-2-oxoethylamino)-2-fluoro-4-methylbenzonitrile (14.19 g, 61.2 mmol). LC/MS (m/z: 233, $M^{+1}$)

Step 3—Preparation of 5-(4-cyclopropyl-2-mercapto-1H-imidazol-1-yl)-2-fluoro-4-methylbenzonitrile—Compound (4)

5-(2-Cyclopropyl-2-oxoethylamino)-2-fluoro-4-methylbenzonitrile (14.19 g, 61.2 mmol) was dissolved in glacial acetic acid (300 mL). Potassium thiocyanate (11.9 g, 122.4 mmol) was added as a solid with stirring. The reaction mixture was heated to 110° C. for 4 hours at which time the solvent was removed under reduced pressure. The residue was taken up in dichloromethane (200 mL) and washed with 200 mL water. The aqueous extract was extracted with (2×200 mL) additional dichloromethane, the organic extracts combined and dried over magnesium sulfate. The solvent was removed under reduced pressure and the oily residue was re-dissolved in EA (50 mL) and 150 mL hexanes was added. A dark layer formed and a stir bar was added to the flask. Vigorous stirring caused the product to precipitate as a peach colored solid. The product was collected by filtration, to yield 5-(4-cyclopropyl-2-mercapto-1H-imidazol-1-yl)-2-fluoro-4-methylbenzonitrile, (14.26 g, 52.23 mmol). Anal. LC/MS (m/z: 274, $M^{+1}$)

Step 4—Preparation of 5-(4-cyclopropyl-1H-imidazol-1-yl)-2-fluoro-4-methylbenzonitrile—Compound (5)

In a 500 mL three neck round bottom flask was placed acetic acid (96 mL), water (19 mL) and hydrogen peroxide (30%, 7.47 mL, 65.88 mmol). The mixture was heated to 45° C. with stirring under nitrogen while monitoring the internal temperature. 5-(4-Cyclopropyl-2-mercapto-1H-imidazol-1-yl)-2-fluoro-4-methylbenzonitrile (6.00 g, 21.96 mmol) was then added as a solid in small portions over 30 minutes while maintaining an internal temperature below 55° C. When addition of the thioimidazole was complete the reaction was stirred for 30 minutes at a temperature of 45° C., and then cooled to room temperature, and a solution of 20% wt/wt sodium sulfite in water (6 mL) was slowly added. The mixture was stirred for 30 minutes and solvents were removed under reduced pressure. The residue was suspended in 250 mL of water and 4N aqueous ammonium hydroxide was added to bring the pH to ~10. The mixture was extracted with dichloromethane (3×200 ml), the organics combined, dried over magnesium sulfate, and the solvent was removed under reduced pressure. The residue was dissolved in 20 mL EA, and 80 mL of hexanes were added with stirring. The solvents were decanted off and an oily residue was left behind. This process was repeated and the product, 5-(4-cyclopropyl-1H-imidazol-1-yl)-2-fluoro-4-methylbenzonitrile was obtained as a viscous oil (5.14 g, 21.33 mmol) Anal. LC/MS (m/z: 242, $M^{+1}$)

Step 5—Preparation of 5-(4-cyclopropyl-1H-imidazol-1-1-2-fluoro-4-methylbenzoic acid hydrochloride (6)

5-(4-Cyclopropyl-1H-imidazol-1-yl)-2-fluoro-4-methylbenzonitrile (11.21 g, 46.50 mmol) was placed in a round bottom flask fitted with a reflux condenser, and suspended in 38% hydrochloric acid (200 mL). The mixture was heated to 100° C. for 4.5 hours, and then cooled to room temperature. Solvent was removed under reduced pressure to give a pink solid, to which was added 100 ml of EA. The solid product was collected by filtration and washed with 3×100 mL EA. To the solid product was added 100 mL 10% methanol in dichloromethane, the mixture stirred, and the filtrate collected. This was repeated with 2 more 100 ml portions of 10% methanol in dichloromethane. The filtrates were combined and solvent was removed under reduced pressure, to provide crude 5-(4-cyclopropyl-1H-imidazol-1-yl)-2-fluoro-4-methylbenzoic acid hydrochloride. No further purification was carried out (11.13 g, 37.54 mmol). Anal. LC/MS (m/z: 261, $M^{+1}$)

Step 6—Preparation of 5-(4-cyclopropyl-1H-imidazol-1-yl)-2-fluoro-N-(6-(4-isopropyl-4H-1,2,4-triazol-3-yl)pyridin-2-yl)-4-methylbenzamide—formula (I)

5-(4-Cyclopropyl-1H-imidazol-1-yl)-2-fluoro-4-methylbenzoic acid hydrochloride (1.5 g, 5.07 mmol) was suspended in anhydrous 1,2-dichloromethane (25 mL) at room temperature. Oxalyl chloride (0.575 ml, 6.59 mmol) was added with stirring under nitrogen, followed by N,N-dimethylformamide (0.044 ml, 0.507 mmol). The mixture was stirred for 4 hr at room temperature, and then the solvent was removed under reduced pressure. The residue was dissolved in 25 mL anhydrous dichloromethane. 6-(4-isopropyl-4H-1,2,4-triazol-3-yl)pyridin-2-amine (1.13 g, 5.58 mmol) (compound C) and 4-dimethylaminopyridine (0.62 g, 5.07 mmol) were rapidly added with stirring under nitrogen. The reaction was stirred for 2 hours at room temperature and aqueous saturated $NaHCO_3$ (15 mL) was added. The mixture was stirred for 10 minutes, and the layers were separated, and the aqueous layer was washed 1×20 mL dichloromethane. The combined organics were dried ($MgSO_4$), filtered and concentrated. The residue was dissolved in a minimum amount of $CH_3CN$ and water was slowly added until solids precipitated from the mixture. The solid was collected by filtration and dried to give 5-(4-cyclopropyl-1H-imidazol-1-yl)-2-fluoro-N-(6-(4-isopropyl-4H-1,2,4-triazol-3-yl)pyridin-2-yl)-4-methylbenzamide in ~96% purity (1.28 g, 2.88 mmol). Anal. LC/MS (m/z: 446, $M^{+1}$). The material was further purified by RP-HPLC (reverse phase HPLC) to obtain an analytically pure sample as the HCl salt.

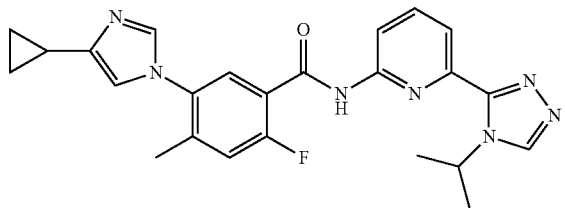 [SMILES: Cc1cc(F)c(C(=O)Nc2cccc(-c3nncn3C(C)C)n2)cc1-n1cnc(C2CC2)c1]

$C_{24}H_{24}FN_7O$—HCl. 446.2 (M+1). $^1$H-NMR (DMSO): δ 11.12 (s, 1H), 9.41 (s, 1H), 9.32 (s, 1H), 8.20 (d, J=8.4 Hz, 1H), 8.07 (t, J=8.4 Hz, 1H), 7.95 (d, J=6.4 Hz, 1H), 7.92 (d, J=7.6 Hz, 1H), 7.79 (s, 1H), 7.59 (d, J=10.4 Hz, 1H), 5.72 (sept, J=6.8 Hz, 1H), 2.29 (s, 3H), 2.00-2.05 (m, 1H), 1.44 (d, J=6.8 Hz, 6H), 1.01-1.06 (m, 2H), 0.85-0.89 (m, 2H).

Biological Assays

ASK1 (Apoptosis Signal-Regulating Kinase 1)
TR-FRET Kinase Assay (Biochemical $IC_{50}$)

The ability of compounds to inhibit ASK1 kinase activity was determined using a time resolved fluorescence resonance energy transfer [TR-FRET] assay utilizing biotinylated myelin basic protein [biotin-MBP] as the protein substrate. A Beckman Biomek FX liquid handling robot was utilized to spot 2 μL/well of compounds in 2.44% aqueous DMSO into low volume 384-well polypropylene plates [Nunc, #267460] to give a final concentration of between 100 μM and 0.5 nM compound in the kinase assay. A Deerac Fluidics Equator was used to dispense 3 μL/well of 0.667 ng/μL [Upstate Biotechnologies, #14-606, or the equivalent protein prepared in-house] and 0.1665 ng/mL biotin-MBP [Upstate Biotechnologies, #13-111] in buffer (85 mM MOPS, pH 7.0, 8.5 mM Mg-acetate, 5% glycerol, 0.085% NP-40, 1.7 mM DTT and 1.7 mg/mL BSA) into the plates containing the spotted compounds.

The enzyme was allowed to pre-incubate with compound for 20 minutes prior to initiating the kinase reaction with the addition of 5 μL/well 300 μM ATP in buffer (50 mM MOPS, pH 7.0, 5 mM Mg-acetate, 1 mM DTT, 5% DMSO) using the Deerac Fluidics Equator. The kinase reactions were allowed to proceed for 20 minutes at ambient temperature and were subsequently stopped with the addition of 5 μL/well 25 mM EDTA using the Deerac Fluidics Equator. The Biomek FX was then used to transfer 1 μL/well of each completed kinase reaction to the wells of an OptiPlate-1536 white polystyrene plate [PerkinElmer, #6004299] that contained 5 μL/well detection reagents (1.11 nM Eu-W1024 labeled anti-phosphothreonine antibody [PerkinElmer, #AD0094] and 55.56 nM streptavidin allophycocyanin [PerkinElmer, #CR130-100] in 1× LANCE detection buffer [PerkinElmer, #CR97-100]). The TR-FRET signal was then read on a Perkin Elmer Envision plate reader after incubating the plates at ambient temperature for 2 hours.

The 100% inhibition positive control wells were generated by switching the order of addition of the EDTA and ATP solutions described above. These wells and 0% inhibition wells containing spots of 2.44% DMSO at the beginning of the assay were used in calculating the % inhibition for the test compounds.

Result

The compound of formula (I) inhibited ASK1 with an $IC_{50}$ of 3.0 nM. This data suggests that the compound of formula (I) is a potent inhibitor of ASK1 in the presence of the competitive ligand ATP.

In an updated version of the assay above, the inhibitory activity of compound of the invention against ASK1 was examined using a TR-FRET ASK1 assay which determined the amount of phosphate transferred to a peptide substrate from ATP.

Materials and Methods

Reagents

Dephosphorylated recombinant human ASK1 kinase was from Gilead Sciences. Small molecule kinase inhibitor staurosporine (Catalogue # S6942) and dithiothreitol (DTT, catalogue #43815-5G) were obtained from Sigma Chemicals (St. Louis, Mo.). ATP (catalogue #7724) was from Affymetrix (Santa Clara, Calif.) and the compound of formula (I) was from Gilead Sciences. HTRF KinEASE™-STK S3 kit was obtained from Cisbio (Bedford, Mass.). All other reagents were of the highest grade commercially available.

Assays

The assay measures the phosphorylation level of a biotinylated peptide substrate by the ASK1 kinase using HTRF detection (6.1). This is a competitive, time-resolved fluorescence resonance energy transfer (TR-FRET) immunoassay, based on HTRF® KinEASE™-STK manual from Cisbio (6.1). Test compound, 1 μM STK3 peptide substrate, 4 nM of ASK1 kinase are incubated with 10 mM MOP buffer, pH. 7.0 containing 10 mM Mg-acetate, 0.025% NP-40, 1 mM DTT, 0.05% BSA and 1.5% glycerol for 30 minutes then 100 □M ATP is added to start the kinase reaction and incubated for 3 hr. Peptide antibody labeled with 1× $Eu^{3+}$ Cryptate buffer containing 10 mM EDTA and 125 nM Streptavidin XL665 are added to stop the reaction and phosphorylated peptide substrate is detected using Envision 2103 Multilabeled reader from PerkinElmer. The fluorescence is measured at 615 nm (Cryptate) and 665 nm (XL665) and a ratio of 665 nm/615 nm is calculated for each well. The resulting TR-FRET level (a ratio of 665 nm/615 nm) is proportional to the phosphorylation level. Under these assay conditions, the degree of phosphorylation of peptide substrate was linear with time and concentration for the enzyme. The assay system yielded consistent results with regard to $K_m$ and specific activities for the enzyme. For inhibition experiments ($IC_{50}$ values), activities were performed with constant concentrations of ATP, peptide and several fixed concentrations of inhibitors. Staurosporine, the nonselective kinase inhibitor, was used as the positive control. All enzyme activity data are reported as an average of quadruplicate determination.

Data Analysis

The $IC_{50}$ values were calculated following equation:

$$y = \text{Range}/\{1+(x/IC_{50})^s\} + \text{Background}$$

Where x and y represent the concentration of inhibitors and enzyme activity, respectively. Enzyme activity is expressed as the amount of Phosphate incorporated into substrate peptide from ATP. Range is the maximum y range (no inhibitor, DMSO control) and s is a slope factor (6.2).

Results

The compound of formula (I) exhibited an IC50 of 3.2 nM under this test condition. The data demonstrates that the compound of formula (I) is a potent inhibitor of the ASK-1 1 receptor.

ASK1 (Apoptosis Signal-Regulating Kinase 1) 293 Cell-Based Assay (Cellular $EC_{50}$)

The cellular potency of compounds was assayed in cells stably expressing an AP-1:luciferase reporter construct (293/AP1-Luc cells—Panomics Inc., 6519 Dumbarton Circle, Fremont, Calif.). Cells were infected with an adenovirus expressing kinase active ASK1 (631-1381 of rat ASK1 cDNA), which will activate the AP-1 transcription factor and increase the expression of luciferase Inhibitors of ASK1 will decrease the enzyme activity of ASK1 and therefore decrease the activity of AP-1 transcription factor and the expression of luciferase.

1. Materials Required for this Protocol

| Media and Reagents | Source Company | Catalog No. |
|---|---|---|
| AP-1 Reporter 293 Stable Cell Line | Panomics | Unknown |
| DMEM (w/ high glucose, w/o L-glutamine, w/ pyruvate, w/ HEPES | MediaTech | 15-018-CM |
| DMEM (w/ high glucose, w/o L-glutamine, w/o pyruvate, w/o HEPES, w/o phenol red | Invitrogen | 31053-028 |
| HEPES, 1M | Invitrogen | 15630-080 |
| Sodium Pyruvate, 100 mM | Invitrogen | 11360-070 |
| Fetal Bovine Serum, "FBS" | Hyclone | SH30088.03 |
| Pen-Strep-Glut., "PSG" | Invitrogen | 10378-016 |
| HygromycinB | Calbiochem | 400052 |
| Dulbecco's PBS (sterile) | MediaTech | 21-030-CM |
| Trypsin-EDTA (0.25%) | Invitrogen | 25200-056 |
| Steady-Glo Luciferase Assay System | Promega | E2550 |

| Labware | Source | Catalog No. |
|---|---|---|
| Flasks (poly-D-Lysine coated, 150 cm², vented cap) | BD Biosciences | 356538 |
| Plates (poly-D-Lysine coated, 384-well, white/clear, sterile TCT) | Greiner (through VWR Scientific) | 781944 (82051-354) |
| White Backing Tape | PerkinElmer | 6005199 |
| Cell Strainers (40 um nylon, blue ring, fits 50 mL conical vials) | VWR Scientific | 21008-949 |

2. Reference Materials
Panomics 293/AP1-Luc stable cell-line product insert.
Promega Steady-Glo Luciferase Assay System product insert.
3. Media Required
Complete Growth Medium, "CGM"
DMEM (MediaTech)
10% FBS
1% PSG
100 ug/mL HygromycinB
Assay Medium, "AM"
DMEM (Invitrogen)
25 mM HEPES
1 mM Sodium Pyruvate
1% PSG
4. Methods
Maintenance:
  293/AP1-Luc Maintain 293/Acells per vendor's instructions; harvest cells at ~80% confluence in T150 flasks as follows:
Aspirate media, wash gently with ~12 mL sterile D-PBS, aspirate.
Add 5 mL Trypsin-EDTA, tilt gently to coat flask, and incubate ~5 min. at 37° C.
Do not tap flask; add 5 mL CGM, wash flask 4× with cell suspension, transfer to 50 mL conical vial, centrifuge 5 min. at 1200 rpm.
Aspirate media from cell pellet, add 20 to 30 mL CGM, resuspend pellet by pipeting 6×, pass through cell strainer to disperse clumps (if necessary), and count cells with hemocytometer.
Assay Day 1:
Harvest cells as above, except resuspend cell pellet.
  Count cells and dilute to $1.5 \times 10^5$ cells per mL; add adenovirus such that there are 5 infectious forming units per cell. Prime (20 to 30 mL) and plate cells in Greiner poly-D-Lysine coated 384-well plates at $1.2 \times 10^4$ cells per well using BioTek uFill (80 uL per well).
Immediately dose plates with 0.4 uL of compound dose series (in 100% DMSO) incubate 24 hours in humidified incubator (37° C., 5% $CO_2$).
Assay Day 2:
  Process plates (per manufacturer's instructions) as follows:
Set plates in laminar flow hood & uncover for 30 minutes at room temperature to cool.
Remove 60 uL of AM from assay wells
Add 20 uL per well Steady-Glo Firefly substrate, let sit for 10-20 minutes at room temperature
Cover bottom of assay plates with white backing tape.
Acquire data on a fluorescence plate reader
The 100% inhibition positive control wells were generated by infecting cells with an adenovirus expressing catalytically inactive ASK1 mutant with lysine to argine mutation at residue 709.

Result
The compound of formula (I) exhibits an $EC_{50}$ of 2.0 nM.
Determination of Kd
Kinase Assays
  Kinase-tagged T7 phage strains were prepared in an *E. coli* host derived from the BL21 strain. *E. coli* were grown to log-phase and infected with T7 phage and incubated with shaking at 32° C. until lysis. The lysates were centrifuged and filtered to remove cell debris. The remaining kinases were produced in HEK-293 cells and subsequently tagged with DNA for qPCR detection. Streptavidin-coated magnetic beads were treated with biotinylated small molecule ligands for 30 minutes at room temperature to generate affinity resins for kinase assays.
  The liganded beads were blocked with excess biotin and washed with blocking buffer (SeaBlock (Pierce), 1% (bovine serum albumin), 0.05% Tween 20, 1 mM DTT (dithiothreitol)) to remove unbound ligand and to reduce non-specific binding. Binding reactions were assembled by combining kinases, liganded affinity beads, and test compounds in 1× binding buffer (20% SeaBlock, 0.17×PBS, 0.05% Tween 20, 6 mM DTT). All reactions were performed in polystyrene 96-well plates in a final volume of 0.135 mL. The assay plates were incubated at room temperature with shaking for 1 hour and the affinity beads were washed with wash buffer (1×PBS, 0.05% Tween 20). The beads were then re-suspended in elution buffer (1×PBS, 0.05% Tween 20, 0.5 μM non-biotinylated affinity ligand) and incubated at room temperature with shaking for 30 minutes. The kinase concentration in the eluates was measured by qPCR.
  Binding constants (Kds) were calculated with a standard dose-response curve using the Hill equation.
Result
  The compound of formula (I) exhibited a $K_d$ of 0.24 nM.
    This data suggests that the compound of formula (I) binds potently to ASK1 receptor in the absence of ATP.
Determination of Percent of Compound Bound to Plasma
Experimental Design:
  1 mL Teflon dialysis cells from Harvard Apparatus (Holliston, Mass., USA) were used in these experiments. Prior to the study, dialysis membrane was soaked for approximately one hour in 0.133 M phosphate buffer, pH 7.4. A nominal concentration of 2 μM of compound was spiked into 1 mL of plasma or 1 mL of cell culture media. The total volume of liquid on each side of the cell was 1 mL. After 3 hours equilibration in a 37° C. water bath, samples from each side of the cell were aliquoted into the appropriate vials containing either 1 mL of human plasma (cell culture media), or buffer. Sample vials were weighed and recorded. A 100 μL aliquot was removed and added to 400 μL quenching solution (50% methanol, 25% acetonitrile, 25% water and internal standard). Samples were vortexed and centrifuged for 15 minutes at 12000 G. 200 μL of the supernatant was removed and placed into a new 96 well plate. An additional 200 μL of 1:1 ACN:water was added. The plate was then vortexed and subjected to LC-MS analysis. The percent unbound for an analyte in plasma was calculated using the following equations $$\% \text{ Unbound} = 100(C_f/C_t)$$

where $C_f$ and $C_t$ are the post-dialysis buffer and plasma concentrations, respectively.
Results
  The percent unbound measured in human plasma for the compound of formula (I) is 11.94%
Determination of CACO-2 Efflux Ratio
Experimental:
  Caco-2 cells were maintained in Dulbecco's Modification of Eagle's Medium (DMEM) with sodium pyruvate, Glutmax supplemented with 1% Pen/Strep, 1% NEAA and 10% fetal bovine serum in an incubator set at 37° C., 90% humidity and 5% $CO_2$. Caco-2 cells between passage 62 and 72 were seeded at 2100 cells/well and were grown to confluence over at least 21-days on 24 well PET (polyethylene-terephthalate) plates (BD Biosciences). The receiver well contained HBSS buffer (10 mM HEPES, 15 mM Glucose with pH adjusted to pH 6.5) supplemented with 1% BSA pH adjusted to pH 7.4. After an initial equilibration with transport buffer, TEER values were read to test membrane integrity. Buffers containing test compounds were added and 100 µl of solution was taken at 1 and 2 hrs from the receiver compartment. Removed buffer was replaced with fresh buffer and a correction is applied to all calculations for the removed material. The experiment was carried out in replicate. All samples were immediately collected into 400 µl 100% acetonitrile acid to precipitate protein and stabilize test compounds. Cells were dosed on the apical or basolateral side to determine forward (A to B) and reverse (B to A) permeability. Permeability through a cell free trans-well is also determined as a measure of cellular permeability through the membrane and non-specific binding. To test for non-specific binding and compound instability percent recovery is determined. Samples were analyzed by LC/MS/MS.

The apparent permeability, $P_{app}$, and % recovery were calculated as follows:

$$P_{app}=(dR/dt) \times V_r/(A \times D_0)$$

$$\% \text{ Recovery}=100 \times ((V_r \times R_{120})+(V_d \times D_{120}))/(V_d \times D_0)$$

where,
dR/dt is the slope of the cumulative concentration in the receiver compartment versus time in µM/s based on receiver concentrations measured at 60 and 120 minutes.
$V_r$ and $V_d$ is the volume in the receiver and donor compartment in $cm^3$, respectively.
A is the area of the cell monolayer (0.33 $cm^2$).
$D_0$ and $D_{120}$ is the measured donor concentration at the beginning and end of the experiment, respectively.
$R_{120}$ is the receiver concentration at the end of the experiment (120 minutes).
Absorption and Efflux Classification:

| | |
|---|---|
| $P_{app}$ (A to B) ≥ 1.0 × $10^{-6}$ cm/s | High |
| 1.0 × $10^{-6}$ cm/s > $P_{app}$ (A to B) ≥ 0.5 × $10^{-6}$ cm/s | Medium |
| $P_{app}$ (A to B) < 0.5 × $10^{-6}$ cm/s | Low |
| $P_{app}$ (B to A)/$P_{app}$ (A to B) ≥ 3 | Significant Efflux |
| % recovery <20% | May affect measured permeability |
| Cell Free $P_{app}$ <15 | May affect measured permeability |

Result

The compound of formula (I) was observed to have a CACO A→B value of 27; and a CACO B→A value of 35 resulting in a efflux ratio (B→A)/(A→B) of 1.3.

Determination of Metabolic Stability in Hepatic Microsomal Fraction:

Experimental:

Metabolic stability was assessed using cofactors for both oxidative metabolism (NADPH) and conjugation (UDP glucuronic acid (UDPGA)). Duplicate aliquots of the compound of formula (I) (3 µL of 0.5 mM DMSO stock) or metabolic stability standards (Buspirone) were added to microsome stock diluted with potassium phosphate buffer, pH 7.4, to obtain a protein concentration of 1.0 mg/mL and containing alamethicin as a permeabilizing agent. Metabolic reactions were initiated by the addition of NADPH regenerating system and UDPGA cofactor. The final composition of each reaction mixture was: 3 µM test compound, 1 mg microsomal protein/mL, 5 mM UDPGA, 23.4 µg/mL alamethicin, 1.25 mM NADP, 3.3 mM glucose-6-phosphate, 0.4 U/mL glucose-6-phosphate dehydrogenase and 3.3 mM $MgCl_2$ in 50 mM potassium phosphate buffer, pH 7.4. At 0, 2, 5, 10, 15, 30, 45, and 60 mM, 25 µL aliquots of the reaction mixture were transferred to plates containing 250 µl of IS/Q (quenching solution containing internal standard). After quenching, the plates were centrifuged at 3000×g for 30 minutes, and 10 µL aliquots of the supernatant were analyzed using LC/MS to obtain analyte/internal standard peak area ratios.

Metabolic stability in microsomal fractions were determined by measuring the rate of disappearance of the compound of formula (I). Data (% of parent remaining) were plotted on a semi logarithmic scale and fitted using an exponential fit:

$$C_t = C_0 \cdot e^{-K \cdot t} \text{ and } T_{1/2}=\ln 2/K \text{ where}$$

$C_t$ % of parent remaining at time=t
$C_0$ % of parent remaining at time=0
t time (hr)
K First order elimination rate constant ($hr^{-1}$)
T½ A In vitro half-life (hr)
The predicted hepatic clearance was calculated as follows {reference 1}:

$$CL_{int} = K \cdot V \cdot Y_P/P \text{ or } CL_{int} = K \cdot V \cdot Y_H/H$$

$$CL_h=(CL_{int} \cdot Q_h)/(CL_{int}+Q_h), \text{ where}$$

$CL_h$ Predicted hepatic clearance (L/hr/kg body weight)
$CL_{int}$ Intrinsic hepatic clearance (L/hr/kg body weight)
V Incubation volume (L)
$Y_P$ Microsome protein yield (mg protein/kg body weight)
$Y_H$ Hepatocyte yield (millions of cells/kg body weight)
P Mass of protein in the incubation (mg)
H Number of hepatocytes in the incubation (million)
$Q_h$ Hepatic blood flow (L/hr/kg body weight)

Predicted hepatic extraction was then calculated by comparison of predicted hepatic clearance to hepatic blood flow. A compound was considered stable if the reduction of substrate concentration was <10% over the course of the incubation (corresponding to an extrapolated half-life of >395 min in microsomal fractions and >39.5 hr in hepatocytes).

Values used for calculation of the predicted hepatic clearance are shown in the tables below:

TABLE 1

Values Used for Calculation of the Predicted Hepatic Clearance from Microsomal Stability

| | Hepatic Microsomes | | | |
|---|---|---|---|---|
| Species | V (L) | P (mg) | Y (mg/kg) | $Q_h$ (L/kg) |
| Rat | 0.001 | 1.0 | 1520 | 4.2 |
| Cynomolgus Monkey | 0.001 | 1.0 | 684 | 1.6 |
| Rhesus Monkey | 0.001 | 1.0 | 1170 | 2.3 |
| Dog | 0.001 | 1.0 | 1216 | 1.8 |
| Human | 0.001 | 1.0 | 977 | 1.3 |

Result:

The predicted hepatic clearance in human as determined from in vitro experiments in microsomal fractions is 0.1 L/h/kg.

Determination of Rat CL and Vss for Test Compounds

Pharmacokinetics of Test Compounds Following a 1 Mg/Kg IV Infusion and 5.0 Mg/Kg PO Dose in Rats Test Article and Formulation For IV administration the test compound was formulated in 60:40 PEG 400:water with 1 equivalent HCl at 0.5 mg/mL. The formulation was a solution.

For PO (oral) administration, the test compound was formulated in 5/75/10/10 ethanol/PG/solutol/water at 2.5 mg/mL. The formulation was a solution.

Animals Used

IV and PO dosing groups each consisted of 3 male SD rats. At dosing, the animals generally weighed between 0.317 and 0.355 kg. The animals were fasted overnight prior to dose administration and up to 4 hr after dosing.

Dosing

For the IV infusion group, the test compound was administered by intravenous infusion over 30 minutes. The rate of infusion was adjusted according to the body weight of each animal to deliver a dose of 1 mg/kg at 2 mL/kg. For the oral dosing group, the test article was administered by oral gavage at 2 mL/kg for a dose of 5.0 mg/kg.

Sample Collection

Serial venous blood samples (approximately 0.4 mL each) were taken at specified time points after dosing from each animal. The blood samples were collected into Vacutainer™ tubes (Becton-Disckinson Corp, New Jersey, USA) containing EDTA as the anti-coagulant and were immediately placed on wet ice pending centrifugation for plasma.

Determination of the Concentrations of the Compound of Formula (I) in Plasma

An LC/MS/MS method was used to measure the concentration of test compound in plasma.

Calculations

Non-compartmental pharmacokinetic analysis was performed on the plasma concentration-time data.

Results

The compound of formula (I) exhibited a CL of 0.09 L/hr/kg; an oral bioavailability of 75%; $t_{1/2}$ of 5.07 hr and a Vss of 0.55 L/kg in rats.

Cyp Inhibition Assay

Objective

To assess the potential of the test compound to inhibit the main cytochrome P450 isoforms, CYP1A, CYP1A2, CYP2B6, CYP2C8, CYP2C9, CYP2C19, CYP2D6 and CYP3A4 (2 substrates).

Cytochrome P450 Inhibition $IC_{50}$ Determination (8 Isoform, 9 Substrates)

Protocol Summary

Test compound (0.1 μM-25 μM) is incubated with human liver microsomes and

NADPH in the presence of a cytochrome P450 isoform-specific probe substrate. For the CYP2B6, CYP2C8, CYP2C9, CYP2C19, CYP2D6 and CYP3A4 specific reactions, the metabolites are monitored by mass spectrometry. CYP1A activity is monitored by measuring the formation of a fluorescent metabolite. A decrease in the formation of the metabolite compared to the vehicle control is used to calculate an IC50 value (test compound concentration which produces 50% inhibition).

Assay Requirements

500 μL of a 10 mM test compound solution in DMSO.

Experimental Procedure

CYP1A Inhibition

Six test compound concentrations (0.1, 0.25, 1, 2.5, 10, 25 μM in DMSO; final DMSO concentration=0.3%) are incubated with human liver microsomes (0.25 mg/mL) and NADPH (1 mM) in the presence of the probe substrate ethoxyresorufin (0.5 μM) for 5 min at 37° C. The selective CYP1A inhibitor, alpha-naphthoflavone, is screened alongside the test compounds as a positive control.

CYP2B6 Inhibition

Six test compound concentrations (0.1, 0.25, 1, 2.5, 10, 25 μM in DMSO; final DMSO concentration=0.3%) are incubated with human liver microsomes (0.1 mg/mL) and NADPH (1 mM) in the presence of the probe substrate bupropion (110 μM) for 5 min at 37° C. The selective CYP2B6 inhibitor, ticlopidine, is screened alongside the test compounds as a positive control.

CYP2C8 Inhibition

Six test compound concentrations (0.1, 0.25, 1, 2.5, 10, 25 μM in DMSO; final DMSO concentration=0.3%) are incubated with human liver microsomes (0.25 mg/mL) and NADPH (1 mM) in the presence of the probe substrate paclitaxel (7.5 μM) for 30 min at 37° C. The selective CYP2C8 inhibitor, montelukast, is screened alongside the test compounds as a positive control.

CYP2C9 Inhibition

Six test compound concentrations (0.1, 0.25, 1, 2.5, 10, 25 μM in DMSO; final DMSO concentration=0.25%) are incubated with human liver microsomes (1 mg/mL) and NADPH (1 mM) in the presence of the probe substrate tolbutamide (120 μM) for 60 min at 37° C. The selective CYP2C9 inhibitor, sulphaphenazole, is screened alongside the test compounds as a positive control.

CYP2C19 Inhibition

Six test compound concentrations (0.1, 0.25, 1, 2.5, 10, 25 μM in DMSO; final DMSO concentration=0.25%) are incubated with human liver microsomes (0.5 mg/mL) and NADPH (1 mM) in the presence of the probe substrate mephenytoin (25 μM) for 60 min at 37° C. The selective CYP2C19 inhibitor, tranylcypromine, is screened alongside the test compounds as a positive control.

CYP2D6 Inhibition

Six test compound concentrations (0.1, 0.25, 1, 2.5, 10, 25 μM in DMSO; final DMSO concentration=0.25%) are incubated with human liver microsomes (0.5 mg/mL) and NADPH (1 mM) in the presence of the probe substrate dextromethorphan (5 μM) for 5 mM at 37° C. The selective CYP2D6 inhibitor, quinidine, is screened alongside the test compounds as a positive control.

CYP3A4 Inhibition (Midazolam)

Six test compound concentrations (0.1, 0.25, 1, 2.5, 10, 25 μM in DMSO; final DMSO concentration=0.26%) are incubated with human liver microsomes (0.1 mg/mL) and NADPH (1 mM) in the presence of the probe substrate midazolam (2.5 μM) for 5 min at 37° C. The selective CYP3A4 inhibitor, ketoconazole, is screened alongside the test compounds as a positive control.

CYP3A4 Inhibition (Testosterone)

Six test compound concentrations (0.1, 0.25, 1, 2.5, 10, 25 μM in DMSO; final DMSO concentration=0.275%) are incubated with human liver microsomes (0.5 mg/mL) and NADPH (1 mM) in the presence of the probe substrate testosterone (50 μM) for 5 min at 37° C. The selective CYP3A4 inhibitor, ketoconazole, is screened alongside the test compounds as a positive control.

For the CYP1A incubations, the reactions are terminated by methanol, and the formation of the metabolite, resorufin, is monitored by fluorescence (excitation wavelength=535 nm, emission wavelength=595 nm). For the CYP2B6, CYP2C9, CYP2C19, CYP2D6, and CYP3A4 incubations, the reactions are terminated by methanol. The samples are then centrifuged, and the supernatants are combined, for the simultaneous analysis of 4-hydroxytolbutamide, 4-hydroxymephenytoin, dextrorphan, and 1-hydroxymidazolam by LC-MS/MS. Hydroxybupropion, 6α-hydroxypaclitaxel and 6β-hydroxytestosterone are analysed separately by LC-MS/MS. Formic acid in deionised water (final concentration=0.1%) containing internal standard is added to the final sample prior to analysis. A decrease in the formation of the metabolites compared to vehicle control is used to calculate an IC50 value (test compound concentration which produces 50% inhibition).

Results

| CYP450 Isoform | Substrate | Metabolite | Calculated $IC_{50}$ (µM) |
|---|---|---|---|
| 1A | Ethoxyresorufin | Resorufin | >25 µM |
| 1A2 | Phenacetin | Acetaminophen | >25 µM |
| 2B6 | Bupropion | Hydroxybupropion | 19.2 µM |
| 2C8 | Paclitaxel | 6α-Hydroxypaclitaxel | 21.6 µM |
| 2C9 | Tolbutamide | 4-Hydroxytolbutamide | >25 µM |
| 2C19 | S-mephenytoin | 4-Hydroxymephenytoin | >25 µM |
| 2D6 | Dextromethorphan | Dextrorphan | 17.7 µM |
| 3A4 | Midazolam | Hydroxymidazolam | 2.7 µM |
| 3A4 | Testosterone | 6β Hydroxytestosterone | 10.5 µM |

General Study Design for the Rat Unilateral Ureter Obstruction (UUO) Model of Kidney Fibrosis.

Male Sprague-Dawley rats were fed normal chow, housed under standard conditions, and allowed to acclimate for at least 7 days before surgery. At the inception of study, rats were placed into weight-matched groups, and administered (2 ml/kg p.o. bid) via oral gavage vehicle, one of four dose levels of compounds (1, 3, 10, or 30 mg/kg). Rats were anesthetized with isoflurane anesthesia on a nosecone, and laparotomy was performed. Rats underwent complete obstruction of the right ureter (UUO) using heat sterilized instruments and aseptic surgical technique. Rats were administered 50 µl Penicillin G (i.m.) immediately post-operatively. Rats were allowed to recover in a clean, heated cage before being returned to normal vivarium conditions. Rats were administered compounds at the dose described above twice daily (at 12 hour intervals) for the subsequent 7 days. On day 7 following surgery, rats were anesthetized with isoflurane and serum, plasma, and urine collected. Animals were then euthanized, the kidneys harvested, and renal cortical biopsies collected for morphological, histological, and biochemical analysis. All tissues for biochemical analysis are flash-frozen in liquid nitrogen and stored at −80° C., tissues for histological analysis were fixed in 10% neutral buffered formalin Renal fibrosis was evaluated by measuring the amount of collagen IV in the kidney by an ELISA method and by examining the accumulation of alpha-smooth muscle actin positive myofibroblasts in the kidney by immunohistochemistry. For the former, a small piece of frozen kidney cortex was transferred homengenized in RIPA buffer then centrifuged at 14000×g for 10 minutes at at 4° C. The supernatant was collected into pre-chilled tubes and the protein concentration was determined. Equivalent amount of total protein were subjected to a Col IV ELISA assay (Exocell) according to the manufacturers instructions.

Formalin fixed and paraffin embedded kidney tissue was stained with an alpha-smooth muscle actin as previously described (Stambe et al., The Role of p38 Mitogen-Activated Protein Kinase Activation in Renal Fibrosis *J Am Soc Nephrol* 15: 370-379, 2004).

Figure 2:
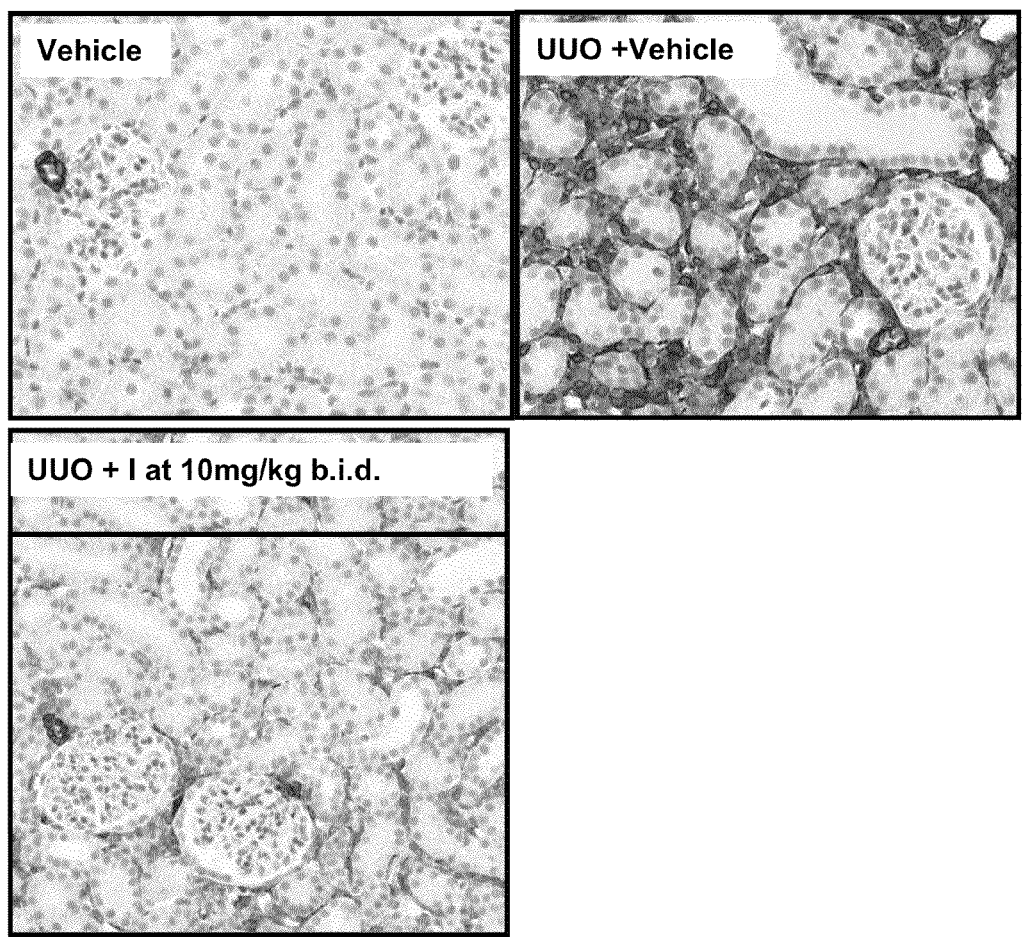
FIG. 2 shows representative images of kidney cortex sections stained with alpha-smooth muscle actin (a marker of activated myofibroblasts) from rats subjected to seven days of unilateral ureteral obstruction and treated with either vehicle, or compound of formula (I) at 1, 3, 10, or 30 mg/kg b.i.d. per day.

Results:

The compound of formula (I) was found to significantly reduce kidney Collagen IV induction (FIG. 1) and accumulation of alpha-smooth muscle positive myofibroblasts (FIG. 2) at doses of 3 to 30 mg/kg.

Comparative Data for Compound of Formula (I) and Reference Compounds

The following table provides comparative results for the compound of formula (I) and the reference compounds A and B disclosed in U.S. Patent publication No. 2001/00095410A1, published Jan. 13, 2011. Applicants note that experiments for which results are compared below were performed under similar conditions but not necessarily simultaneously.

TABLE

| | Compound of formula (I) | Compound A | Compound B |
|---|---|---|---|
| $IC_{50}$ (nM) | 3 | 5 | 6.5 |
| $EC_{50}$ (nM) | 2 | 3.4 | 18 (9X) |
| PBadj $EC_{50}$ (nM) | 17 | 71 (4X) | 563 (33X) |
| CACO (A/B, B/A) | 27/35 | 3.1/18.5 | 0.26/4 |
| Efflux ratio (B/A)/(A/B) | 1.3 | 6.0 | 15.4 |
| fu | 12 | 4.8 | 3.2 |
| Cyp3A4 $IC_{50}$ Testesterone (TST)) (uM) | 11 | 1.1 (10X) | 4 (2.8X) |
| Cyp3A4 $IC_{50}$/PBAdj.$EC_{50}$ | 647 | 15 (43X) | 7 (92X) |
| Vss (L/Kg) in rats | 0.55 | 0.17 (3.2X) | 0.54 |
| CL (L/hr/kg) in rats | 0.11 | 0.30 (2.7X) | 0.39 (3.6X) |
| % F in rats | 75 | 11 (6.8X) | 50 (1.5X) |
| t½ in rats (hr) | 5.07 | 0.59 (8.6X) | 1.3 (3.9X) |

( ) values in parenthesis represent the number of times the compound of formula (I) shows an improvement over the indicated compound for the indicated parameter.

The following can be deduced from the above comparative data:

The compound of formula (I) has an $EC_{50}$ that is comparable to that of Compound A.

The compound of formula (I) has a functional $IC_{50}$ that is comparable to $IC_{50}$, for compounds A and B.

The compound of formula (I) has a protein binding adjusted $EC_{50}$ that is 4 times lower than that of compound A and 33 times lower than that of compound B.

The compound of formula (I) is a weaker Cyp3A4 inhibitor compared to compounds A and B.

The compound of Formula (I) has a CYP3A4 $IC_{50}$/PBAdj.$EC_{50}$ value that is 43 times higher than that for compound of formula A, and 92 times higher than for the compound of formula B.

The compound of formula (I) has a Rat CL value that is 2.7 times lower than that for compound of formula A, and 3.6 times lower than that for the compound of formula B.

The compound of formula (I) has a percent bioavailability in rats that is 6.8 times higher than compound A and 1.5 times higher than compound B.

The compound of formula (I) has a half life in rats that is 8.6 times longer than that of compound A and 3.9 times longer than that of compound B.

The above data fairly suggest that the compound of formula (I) has unexpected and advantageous properties compared to compounds of formula A and B; and that the compound of formula (I) is likely a better candidate for further development for the treatment of chronic kidney disease, lung and/or kidney fibrosis, and/or cardio-renal diseases.

What is claimed is:

1. A method of treating a inhibiting kidney disease fibrosis comprising administering to a patient in need thereof a therapeutically effective amount of a compound of formula (I)

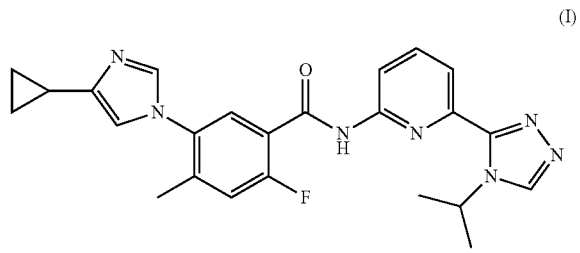 [SMILES: Cc1cc(F)c(C(=O)Nc2cccc(-c3nncn3C(C)C)n2)cc1-n1cnc(C2CC2)c1]

(I)

or a pharmaceutically acceptable salt thereof.

2. The method of claim 1, wherein the kidney-disease fibrosis is associated with diabetic kidney disease.

3. The method of claim 1, wherein the pharmaceutically acceptable salt is the hydrochloride salt.

4. The method of claim 1, wherein the therapeutic amount ranges from 1 mg to 250 mg.

5. The method of claim 1, wherein the compound of formula (I) or a pharmaceutically acceptable salt thereof is administered orally.

6. The method of claim 1, wherein the compound of formula (I) or a pharmaceutically acceptable salt thereof is administered in a single or multiple doses.

7. The method of claim 1, wherein the compound of formula (I) or a pharmaceutically acceptable salt thereof is administered in combination with other therapeutic agents.

8. The method of claim 7, wherein the one or more therapeutic agents is selected from the group consisting of angiotensin converting enzyme inhibitors, angiotensin II receptor blockers, antihypertensive agents, antibiotic agents, analgesic agents, antidepressant agents, or antianxiety agents.

9. The method of claim 7, wherein the pharmaceutical composition and the one or more therapeutic agents are administered simultaneously.

10. The method of claim 7, wherein the pharmaceutical composition and the one or more therapeutic agents are administered one after the other within intervals.

11. A method of treating fibrosis in a kidney comprising administering to a patient in need thereof a pharmaceutical composition comprising a compound of formula (I)

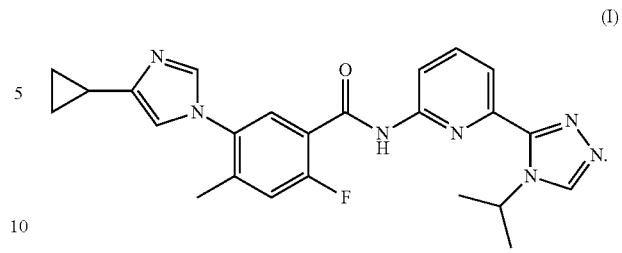

(I)

or a pharmaceutically acceptable salt thereof.

12. The method of claim 11, wherein the pharmaceutically acceptable salt is the hydrochloride salt.

13. The method of claim 11, wherein the pharmaceutical composition further comprises one or more pharmaceutically acceptable carriers.

14. The method of claim 11, wherein the pharmaceutical composition is prepared for delivery as solid tablets.

15. The method of claim 11, wherein the pharmaceutical composition is administered in a single or multiple doses.

16. The method of claim 15, wherein the dose comprises 1 mg to 250 mg of the compound of formula (I).

17. The method of claim 11, wherein the pharmaceutical composition is administered orally.

18. The method of claim 11, wherein the pharmaceutical composition is administered in combination with one or more therapeutic agents.

19. The method of claim 18, wherein the one or more therapeutic agents is selected from the group consisting of angiotensin converting enzyme inhibitors, angiotensin II receptor blockers, antihypertensive agents, antibiotic agents, analgesic agents, antidepressant agents, or antianxiety agents.

20. The method of claim 18, wherein the pharmaceutical composition and the one or more therapeutic agents are administered simultaneously.

21. The method of claim 18, wherein the pharmaceutical composition and the one or more therapeutic agents are administered one after the other within intervals.

* * * * *